(12) United States Patent
Adams

(10) Patent No.: US 8,480,700 B2
(45) Date of Patent: *Jul. 9, 2013

(54) FULL THICKNESS RESECTION DEVICE

(75) Inventor: Ronald D. Adams, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/299,092

(22) Filed: Nov. 17, 2011

(65) Prior Publication Data

US 2012/0065657 A1   Mar. 15, 2012

Related U.S. Application Data

(63) Continuation of application No. 11/940,561, filed on Nov. 15, 2007, now Pat. No. 8,062,318, which is a continuation of application No. 10/453,367, filed on Jun. 3, 2003, now Pat. No. 7,300,445, which is a continuation of application No. 09/994,518, filed on Nov. 26, 2001, now Pat. No. 6,605,078.

(51) Int. Cl.
*A61B 17/32* (2006.01)

(52) U.S. Cl.
USPC ............................................. 606/187

(58) Field of Classification Search
USPC ............... 604/109; 606/105, 106, 167, 172, 606/173
See application file for complete search history.

(56) References Cited

U.S. PATENT DOCUMENTS

| | | | | |
|---|---|---|---|---|
| 5,395,030 A | * | 3/1995 | Kuramoto et al. | 227/179.1 |
| 5,398,670 A | * | 3/1995 | Ortiz et al. | 600/114 |
| 5,586,968 A | * | 12/1996 | Grundl et al. | 600/114 |
| 6,517,477 B1 | * | 2/2003 | Wendlandt | 600/114 |
| 6,605,078 B2 | * | 8/2003 | Adams | 606/1 |
| 7,300,445 B2 | * | 11/2007 | Adams | 606/167 |
| 8,062,318 B2 | * | 11/2011 | Adams | 606/167 |

* cited by examiner

*Primary Examiner* — Kevin T Truong
*Assistant Examiner* — Christopher Beccia
(74) *Attorney, Agent, or Firm* — Fay Kaplun & Marcin, LLP

(57) ABSTRACT

A system for treating a target tissue includes (a) an instrument head sized and shaped for insertion into a hollow organ of a living body, the instrument head including a working chamber movable between an open position in which the working chamber is exposed to an exterior of the head and a closed position in which the working chamber is substantially sealed with respect to an exterior of the instrument head, the instrument head including a first imaging device having a field of view extending distally of a distal end thereof and a second imaging device having a field of view within the working chamber; (b) a handle which, during use, remains outside the living body, the handle including an actuator; (c) a steering mechanism coupled to the actuator for steering the instrument head within the hollow organ based on actuation of the actuator; and (d) a controller coupled to the first and second imaging devices for processing the image data received from the first and second imaging devices and providing images to an operator.

11 Claims, 5 Drawing Sheets

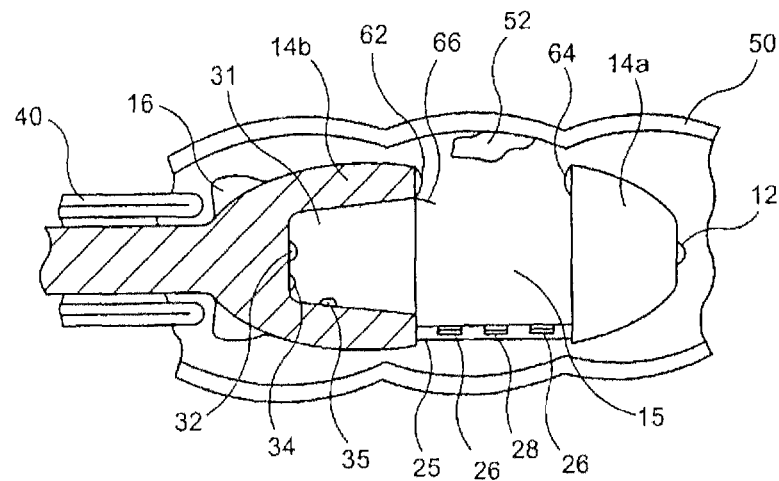
F I G. 3
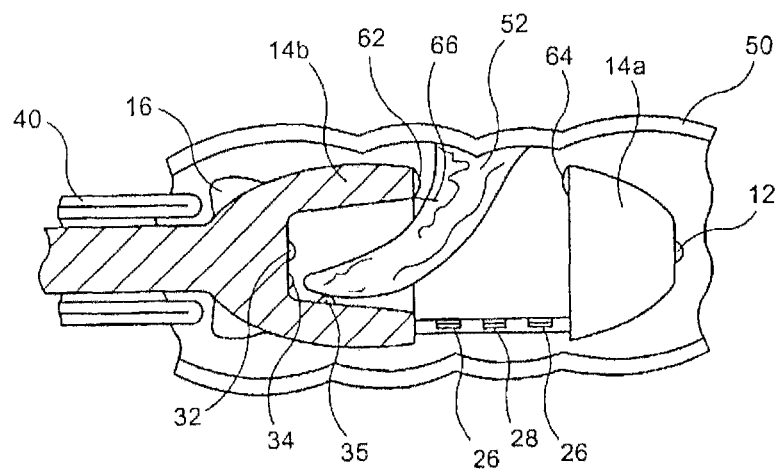
F I G. 4

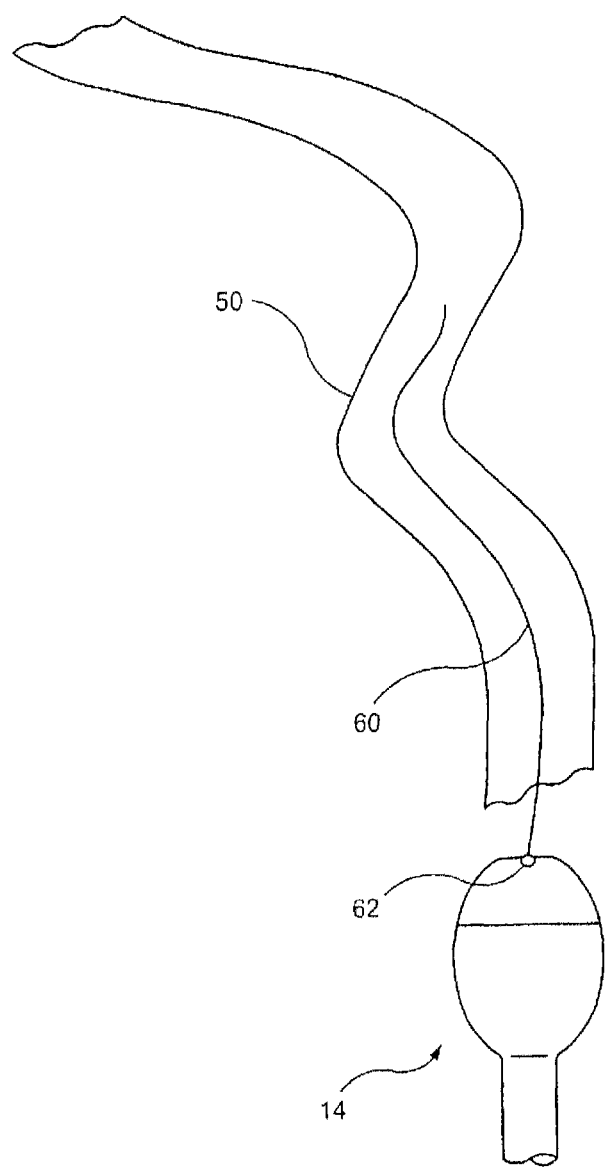
F I G. 6a

FULL THICKNESS RESECTION DEVICE

PRIORITY CLAIM

The present application is a Continuation of U.S. patent application Ser. No. 11/940,367 filed on Nov. 15, 2007 (now U.S. Pat. No. 8,062,318) which is a Continuation of U.S. patent application Ser. No. 10/453,367 filed Jun. 3, 2003, (now U.S. Pat. No. 7,300,445) which is a Continuation of U.S. patent application Ser. No. 09/994,518 filed Nov. 26, 2001 (now U.S. Pat. No. 6,605,078). These patents are expressly incorporated herein, in their entirety, by reference.

FIELD OF THE INVENTION

The present invention relates to full thickness resection devices for performing localized resections of lesions.

BACKGROUND OF THE INVENTION

Resection procedures involve excising a portion of an organ, approximating the surrounding tissue together to close up the hole created by the excision, and removing excess tissue. Various conventional devices and procedures are available for resectioning lesions in organs.

For example, several known resection devices and procedures require at least one incision in an area near the portion of the organ to be excised for access to the lesion or treatment site (because, for example, these resectioning devices may lack steering and/or viewing capabilities). Thus, an incision is required to allow a physician to access the organ section to be excised and guide the device to that section. Alternatively, when the organ section to be excised is beyond the reach of the surgical device, or if the surgical device is not flexible enough to wind through the organ to the site to be excised, an incision is required to position the device for the procedure. Of course, these incisions are painful and may involve a partial or entire loss of mobility while recuperating from the incision, in addition to the discomfort associated with the resectioning procedure itself. In addition, these incisions may add significantly to the recovery time required for the procedure.

One type of conventional resection procedure utilizes a circular stapling instrument in which a tubular section of a substantially tubular organ is excised, resulting in the organ being separated into first and second segments. The open ends of these first and second segments are then tied in a pursestring fashion, approximated toward one another and stapled together. The tissue radially inside the stapled areas (i.e., the "purse-stringed" end sections) is then cut off to open the interiors of the two segments to one another. In this full circle resectioning procedure, at least one incision must be made near the section to be excised in order to cut and "purse string" the end sections of the first and second segments. Also, a second incision is necessary to place one part of the resectioning device in the first segment and a corresponding second part of the device in the second segment. Thus, this type of resectioning procedure involves the drawbacks mentioned above in regard to procedures requiring invasive incisions. In addition, the separation of the organ into two segments creates the risk of spillage of non-sterile organ contents into the sterile body cavity, which may cause severe infection and possibly death.

An alternative resectioning device includes a stapling and cutting assembly on a shaft which may be bent or formed into a desired shape and then inserted into a patient's body cavity. Once the shaft has been bent into the desired shape, the rigidity of the shaft ensures that the shape is maintained throughout the operation. This arrangement limits the effective operating range of the device as the bending of the shaft into the desired shape before insertion and the rigidity of the shaft once bent require the physician to ascertain the location of the organ section to be removed before insertion, and deform the shaft accordingly. Furthermore, the rigidity of the shaft makes it difficult to reach remote areas in the organ—particularly those areas which must be reached by a winding and/or circuitous route (e.g., sigmoid colon). Thus, an incision may be required near the organ section to be excised in order to position such a device at the organ section to be excised.

A full-thickness resection system has been disclosed by the present Applicant along with others in U.S. Pat. No. 6,126, 058, the disclosure of which is expressly incorporated herein by reference in its entirety. The system utilizes a flexible endoscope slidably received through at least a portion of a stapling mechanism.

SUMMARY OF THE INVENTION

The present invention is directed to an operating head for a full thickness resection device, comprising a first optical device disposed on a distal portion thereof, the first optical device having a viewing area extending distally of the distal portion and a second optical device mounted within a working chamber extending within an exterior wall of the operating head, wherein a first portion of the exterior wall is moveable with respect to a second portion thereof to selectively open the working chamber to an exterior of the operating head.

BRIEF DESCRIPTION OF THE DRAWINGS

FIG. 3 shows a side view, in partial cross section, of the full thickness resection device shown in FIG. 1, where the device is in the open position;

FIG. 4 shows a side view, of the full thickness resection device as shown in FIG. 3, where a lesion has been pulled into the device;

FIG. 6a shows a side view of a device according to a further embodiment of the invention moving through a body organ along a guide wire;

FIG. 6b shows a cross-sectional front view of the device according to FIG. 6a;

DETAILED DESCRIPTION

Figure 1:
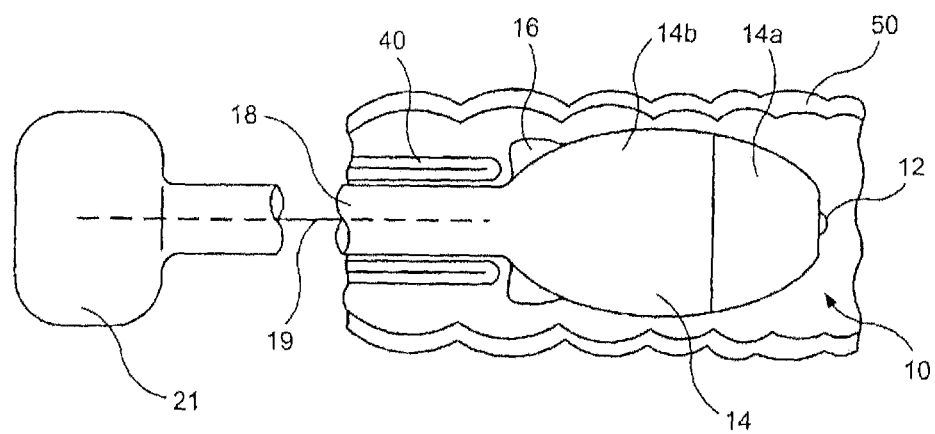
FIG. 1 shows a side view of a full thickness resection device according to one embodiment of the present invention.
Figure 2:
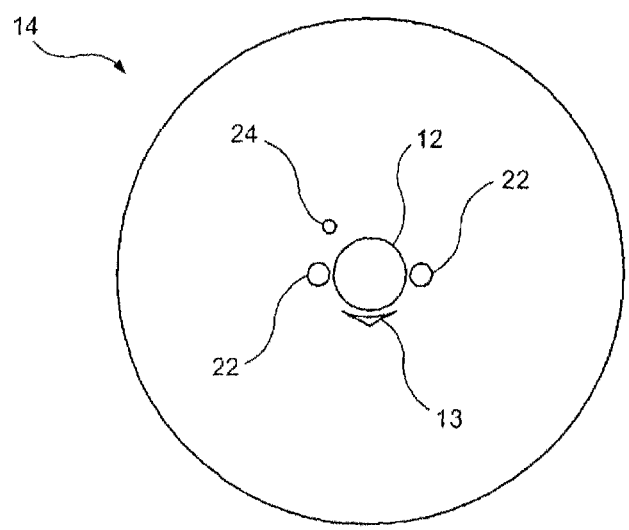
FIG. 2 shows a front view of the full thickness resection device shown in FIG. 1.

As shown in FIGS. 1 and 2, an optical full thickness resection device 10 according to one embodiment of the present invention includes an openable instrument head 14 which is preferably formed from a front portion 14a and a rear portion 14b. The head 14 may be egg-shaped as shown in FIG. 1. Such a shape allows for the head 14 to be smoothly inserted into and removed from an organ 50. However, it is understood that many other shapes of the head 14 may be employed to ease insertion and removal from the organ 50. For example, the head 14 may be bullet-shaped or, alternatively, may be relatively more spherical. In the illustrated embodiment, the head 14 may preferably have a diameter in the range of 10 to 35 mm.

Those skilled in the art will recognize that the organ 50 may include the colon, the small bowel, the esophagus, or a variety of other organs in which endoscopic procedures have been conducted.

Conventional endoscopes employed with prior endoscopic full thickness resection devices incorporated certain functional limitations which frustrated attempts to reduce their size. These devices were employed in a wide variety of procedures and included features which were not utilized in the full thickness resection procedure. For example, these endoscopes included one or more working channels through which an operator might perform therapeutic and/or diagnostic tasks. Furthermore, these endoscopes may also incorporate an insertion tube shaft to enable the operator to push the endoscope through a body lumen. These working channels and the insertion tube add significantly to the diameter of the endoscope. As discussed below, the present invention proposes an endoscope-like device in which these elements are eliminated as unnecessary to the full thickness resectioning procedure.

FIG. 2 shows a cross-sectional view of the front end of a front portion 14a, including additional features of the device 10. In one embodiment, a movable optic device 12 and an irrigation source 13 are provided on the front portion 14a with the optic device 12 providing an interior view of the organ 50 to an operator of the device 10. The irrigation source 13 allows a solution such as saline to be introduced into the organ 50 in order to clear debris therefrom improve the operator's view. Additionally provided are light sources 22 for illuminating the organ 50 so that the optic device 12 captures a satisfactory image for the operator. In one embodiment, the optic device 12 may include a vision chip which may include, for example, both photosensors and parallel processing elements. According to an exemplary embodiment of the device 10, an infusion port 24 allows the operator to inject air or an inert gas into the organ 50 to insufflate the organ. This insufflation of the organ 50 may further improve the operator's view by distending the walls of organ 50.

In the illustrated embodiment, an insertion sheath 40 serves to propel the head 14 through tubular organ 50. In this instance, the insertion sheath 40 which may be formed of a flexible polymeric material such as, for example, polypropylene, is part of an insertion sheath propulsion system and constructed, for example, as described in U.S. Pat. Nos. 5,259,364 and 5,586,968 to Bob et al., the entire disclosures of which are hereby incorporated by reference. The insertion sheath 40 is slidably received around an insertion tube 18 which is of reduced diameter relative to the head 14.

Figure 7:
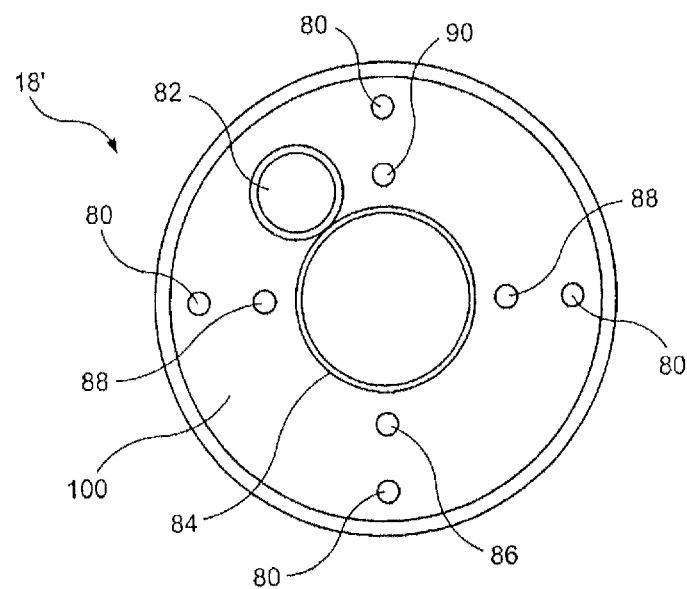
FIG. 7 shows a cross-sectional view of an insertion sheath including an integral custom endoscope according to one embodiment of the present invention.

As described more fully below in regard to FIG. 7, the insertion tube 18' may preferably be constructed substantially similarly to known endoscopes including similar steering and other operating mechanisms but with a reduced diameter with respect to these known endoscopes as no insertion tube is required. Those skilled in the art will understand that the diameter of the insertion tube 18' may be further reduced if no working channels are required therein. That is, although FIG. 7 shows a single working channel 72, for certain operations this working channel 72 may be unnecessary. Thus, an insertion tube 18' for use in such operations may include an integral endoscope 100 with no such working channel 72 and the diameter of the endoscope 100 (and, consequently, that of the insertion tube 18', may be further reduced.

If a propulsion system is to be used, the column strength of the insertion tube 18 may be substantially reduced as the column strength necessary to allow a standard endoscope to be pushed through an organ is no longer necessary. Furthermore, as the insertion tube 18 is received within the insertion sheath 40, no separate insertion tube shaft is incorporated therein as would be the case in a standard endoscope, thereby enabling the diameter of the insertion tube 18 to be further reduced with respect to conventional endoscopes. Thus, the diameter of the insertion tube 18 may preferably be in the range of 5 to 25 mm with an outer diameter of the insertion sheath 40 being between 10 and 30 mm. Of course, those skilled in the art will understand that these values may be made larger or smaller as desired so long as the flexibility and steering capacity of the insertion tube 18 in conjunction with the insertion sheath 40 substantially matches that of conventional endoscopes.

The insertion sheath 40 is longitudinally flexible so as not to impair the flexibility of the insertion tube 18 and the steerability of the device 10 generally. Thus, when a distal end of the insertion sheath 40 abuts against a proximal end of the head 14 and an operator engages the insertion sheath 40 distally into the organ 50, the head 14 is advanced further into the organ 50.

Figure 6B:
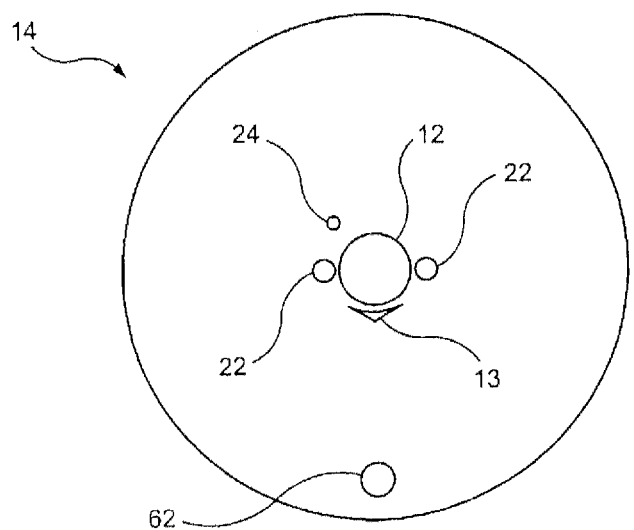

However, it is understood that other propulsion arrangements may be used with the device 10. For example, a crawler system (not shown) may be used to move head 14. Such a crawler system may be constructed, for example, as described in U.S. Pat. No. 5,398,670 to Ortiz et al., and U.S. Pat. No. 5,906,591 to Dario et al. the entire specifications of which are hereby incorporated by reference. In yet another embodiment as shown in FIGS. 6a and 6b, a guidewire 60 is placed in the organ 50 using a conventional endoscope as is known in the art. The guidewire 60 is then strung through the device 10 via a guidewire opening 62 at the front portion 14a of head 14 and the device 10 is pushed along the guidewire 60 to the desired location within the organ 50. In order to accommodate the force exerted on the device 10 as it is pushed into the organ 50, the insertion tube of the device 10 according to this embodiment is formed with an increased column strength relative to embodiments in which a propulsion system is employed.

As shown in FIGS. 3 and 4, in one embodiment, fins 16 are disposed at a proximal end of rear portion 14b. Preferably two or more fins 16 are provided on opposing sides (180° degrees apart) of the rear portion 14b. Alternatively, one fin 16 may be used. The fins 16 provide a solid surface against which the insertion sheath 40 may abut to push device 10 through the organ 50. Also, the fins 16 serve to prevent portions of the tubular organ 50 from becoming entangled with the insertion sheath 40.

Now turning to FIG. 3, the head 14 is shown in an open position in which the front portion 14a is slid forward to expose an interior work area 15. A main optic device 32 is provided at the rear of the rear portion 14b. Preferably, the device 32 points in a generally forward direction as shown in FIG. 3. A base portion 25 of the interior work area 15 may include an auxiliary optic device 26 that points in a direction generally perpendicular to the direction of main device 32. The optic devices 32 and 26 may be illuminated by illumination sources 34 and 28, respectively, to help provide a satisfactory image for the operator. As with the exterior optic device 12, the optic devices 32 and 26 may preferably include vision chips. As will be discussed in connection to the operation of the device 10, the multiple viewing angles provided by the optic devices 32 and 26 allow for an improved method of resectioning tissue. In a preferred embodiment, a suction lumen 36 extends from the proximal end of the device 10 to a port 35 that opens into the work area 15 so that, when suction is drawn therethrough, tissue adjacent to the head 14 is drawn into the work area 15. An anvil 64 is positioned in the work area 15 to work in conjunction with a stapler 62 for stapling tissue received therein. Furthermore, a knife 66 is movably mounted within the work area 15 to cut tissue received therein radially inward with respect to a perimeter of staples delivered by the stapler 62.

A controller 21 is also provided for controlling each of the components discussed above. The controller 21, which may be used by the operator as a handle, may include a plurality of actuators coupled to the head 14 and, in turn, to the various components thereof by a one or more wires or flexible drive cables 19 as would be understood by those of skill in the art. The cables 19 may pass through the insertion tube 18 and into the head 14. Alternatively, the actuators of the controller 21 may be coupled to these components by electric cables and/or by means of remote control (e.g., radio transmission) to actuate electric motors, as would be understood by those of skill in the art, to drive the components as desired by the operator. By manipulating the actuators of the controller 21, the operator may, for example, adjust the optic devices 26 and 32, the illumination sources 28 and 34 as well as any other components of the head 14.

Figure 5A:
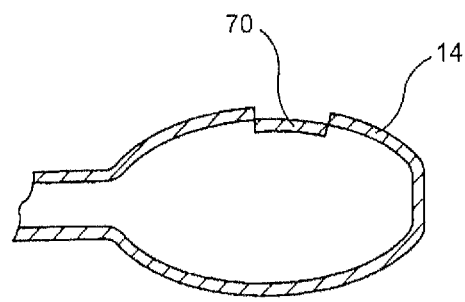
FIG. 5a shows a schematic cross-sectional view of a full thickness resection device having a movable door, according to another embodiment of the invention.
Figure 5B:
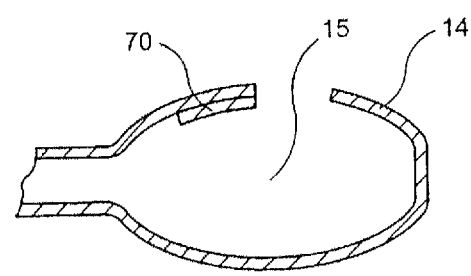
FIG. 5b shows a schematic cross-sectional view of a full thickness resection device as shown in FIG. 5a where the movable door is in the open position.

In an alternative embodiment of the invention shown in schematic views in FIGS. 5a and 5b, the head 14 includes a door 70 instead of the separable front and rear portions 14a and 14b of the previously described embodiment. The door 70 is movable between open and closed positions so that, in the open position, the interior of the organ 50 is accessible to the interior work area 15, as described in the previously described embodiment. With the exception of this difference the apparatus according to this embodiment may function substantially similarly to the other embodiments.

In operation, the head 14 is maintained in the closed position, as shown in FIG. 1, while the device 10 is being maneuvered to the desired location within the organ 50. When the desired location has been found using the exterior optic device 12, with the aid of illumination from light source 22, to view the interior of the organ 50. As described above, to further aid in locating the site, an operator may wash debris away from areas being viewed using the irrigation source 13 and/or by insufflating the organ 50. As described above, resectioning at this desired location may be necessary due to, for example, the presence of a lesion 52 as shown on the wall of the organ 50 in FIGS. 3 and 4.

Once the head 14 has been positioned as required, the interior work area 15 may be exposed by sliding the front portion 14a away from the rear portion 14b of the head 14 using the controller 21. In this position, the optic device 26 on the base portion 25 may be used to view the lesion 52. Moreover, the light source 28 provides the portion of organ 50 with the necessary illumination to provide a satisfactory image to the operator. The operator then draws a partial vacuum in the work area 15 through the use of the suction device 35 to draw the lesion 52 into the work area 15 under visual control of the operator via the optic device 32 and the light source 34. Based on this observation, the operator may also reposition or reorient the head 14, as required. However, once the lesion 52 has been sufficiently drawn into the resectioning chamber 31, the view from the optic device 32 may be obscured by the lesion 52 itself. At this time, the optic device 26 may be used to provide continuing observation of the lesion 52 and its geometry with respect to the organ 50.

The tissue surrounding the lesion 52 may now be stapled using the stapler 62 in conjunction with the anvil 64 and, after the stapling operation has been completed, the knife 66 may be actuated to cut the lesion 52 from the organ 50. The operator then utilizes the controller 21 to slide the front portion 14a toward the rear portion 14b of the head 14 until the head 14 is sealed in the closed position. The lesion 52 is then retained within the work area 15 until the head 14 has been removed from the patient's body, at which time it may be further studied to aid in the patient's diagnosis and/or treatment.

As shown in FIG. 7, an insertion tube 18' according to a first embodiment of the invention may include an integral endoscope 100. The custom endoscope 100 includes a steering mechanism which include control wire guides 80 (in this case 4 guides 80) which are coupled to a distal tip of the integral endoscope 100 as is known in the art. In addition, the integral endoscope 100 includes a single, optional working channel 82, an optic member 84, an irrigation channel 86, one or more light source members 88 (in this case 2 light source members 88) and a suction/insufflation lumen 90. As would be understood by those of skill in the art, the optic member 84 may be either a fiber optic cable or an electric cable depending on the type of optic system employed. Similarly, the light source members 88 may be fiber optic light cables or electric cables if, for example, one or more LED light source members are employed at the distal tip of the integral endoscope 100 to illuminate a viewing area of the optic member 84. Those skilled in the art will understand that the irrigation channel may be employed to supply irrigation fluid to a distal end of the optic member 84 (e.g., a lens) to clean the distal end to maintain the field of vision for an operator of the device.

Figure 8:
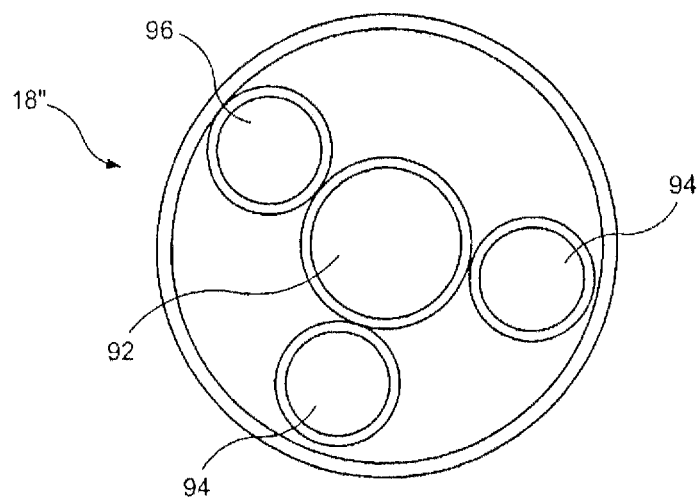
FIG. 8 shows a cross-sectional view of an insertion sheath including an endoscope receiving lumen according to a further embodiment of the present invention.

FIG. 8 shows an alternate embodiment of an insertion tube 18". The insertion tube 18" includes a central endoscope receiving lumen 92, optional working channels 94 and a suction/insufflation lumen 96. Thus, this insertion tube 18" may be employed with a custom endoscope (not shown) constructed substantially as shown in FIG. 7 including an optic member, an irrigation channel and light source members. As the insertion tube 18" includes working channels 94 and the suction/insufflation lumen 96, these items may be eliminated from the custom endoscope for use with this insertion tube 18" thereby reducing the diameter of the endoscope. The use of this insertion tube 18" allows the custom endoscope inserted through the endoscope receiving lumen 92 to be reused, as would be understood by those of skill in the art.

Those skilled in the art will further appreciate that while the apparatus of the present invention has been described with reference to a full thickness resection of the colon, the apparatus may be utilized in other digestive tract transluminal procedures, and may be introduced transorally as well as transanally. Also, while certain embodiments have been described with reference to custom endoscopes, it will be appreciated that the specific configurations of the custom endoscopes/stapler embodiments may be varied. For example, different arrangements of lumena and control wires, and different coupling means for coupling the control wires to the driving gears may be provided with similar results obtained. Also, the control wires may be replaced, for example with flexible cables or hydraulic fluid channels. It will therefore be appreciated by those skilled in the art that yet other modifications could be made to the provided invention without deviating from its spirit and scope as so claimed.

What is claimed is:

1. A system for treating a target tissue, comprising:
an instrument head sized and shaped for insertion into a hollow organ of a living body, the instrument head including a working chamber movable between an open position in which the working chamber is exposed to an exterior of the head and a closed position in which the working chamber is substantially sealed with respect to an exterior of the instrument head, the instrument head including a first imaging device having a field of view extending distally of a distal end thereof and a second imaging device having a field of view within the working chamber;
a handle which, during use, remains outside the living body, the handle including an actuator;
a steering mechanism coupled to the actuator for steering the instrument head within the hollow organ based on actuation of the actuator; and
a controller coupled to the first and second imaging devices for processing the image data received from the first and second imaging devices and providing images to an operator.

2. The system according to claim 1, wherein the first and second imaging devices include at least one of a vision chip and a photosensor.

3. The system according to claim 1, further including:
a light source coupled to the controller for illuminating an interior of the hollow organ.

4. The system according to claim 1, further including:
an insufflation source coupled to the controller for insufflating the hollow organ.

5. The system according to claim 1, further including:
a propulsion system coupled to the controller for propelling the instrument head through the hollow organ.

6. The system according to claim 1, further including:
an irrigation source coupled to the controller for irrigating debris from the first and second optic members.

7. The system according to claim 1, further including:
a suction source coupled to the controller for drawing the target tissue into the working chamber.

8. The system according to claim 1, further including:
a resectioning device coupled to the controller for resectioning the target tissue within working chamber of the instrument head.

9. A system for treating a target tissue, comprising:
an instrument head sized and shaped for insertion into a hollow organ of a living body, the instrument head including a working chamber movable between an open position in which the working chamber is exposed to an exterior of the head and a closed position in which the working chamber is substantially sealed with respect to an exterior of the instrument head, the instrument head including a first imaging device having a field of view extending distally of a distal end thereof and a second imaging device having a field of view within the working chamber;
a steering mechanism coupled to an actuator for steering the instrument head within the hollow organ based on actuation of the actuator;
a controller coupled to the first and second imaging devices for processing the image data received from the first and second imaging devices and providing images to an operator; and
a propulsion system coupled to the instrument head to move the instrument head distally into the hollow organ until the instrument head has reached a desired position within the hollow organ.

10. The system according to claim 9, wherein the propulsion system includes one of a crawler and a guidewire.

11. The system according to claim 9, further including:
a flexible insertion tube for receiving the instrument head over a distal end of the flexible insertion tube; and
a flexible sheath slidably received around the flexible insertion tube, wherein the propulsion system engages the instrument head with a distal end of the flexible sheath to propel the instrument head into the hollow organ.

* * * * *